(12) United States Patent
Mennen et al.

(10) Patent No.: US 7,893,298 B2
(45) Date of Patent: Feb. 22, 2011

(54) METHOD FOR CONCENTRATING AN AQUEOUS AMMONIUM CARBAMATE STREAM

(75) Inventors: Johannes Henricus J. H. Mennen, Meijel (NL); Tjay Tjien T. T. Tjioe, Sittard (NL)

(73) Assignee: Stamicarbon B.V., Sittard (NL)

( * ) Notice: Subject to any disclaimer, the term of this patent is extended or adjusted under 35 U.S.C. 154(b) by 138 days.

(21) Appl. No.: 11/919,991

(22) PCT Filed: May 15, 2006

(86) PCT No.: PCT/NL2006/000249

§ 371 (c)(1),
(2), (4) Date: Mar. 21, 2008

(87) PCT Pub. No.: WO2006/121332

PCT Pub. Date: Nov. 16, 2006

(65) Prior Publication Data

US 2009/0069597 A1    Mar. 12, 2009

(30) Foreign Application Priority Data

May 13, 2005    (NL) .................................... 1029038

(51) Int. Cl.
*C07C 269/00*    (2006.01)
*C07C 51/15*    (2006.01)
(52) U.S. Cl. ...................................... 562/555; 562/550
(58) Field of Classification Search ................ 562/550, 562/555; 564/67, 70, 71, 72
See application file for complete search history.

(56) References Cited

U.S. PATENT DOCUMENTS 6,914,157 B2 * 7/2005 Lardinois .................... 562/550

FOREIGN PATENT DOCUMENTS

DE            1 468 207        11/1968

(Continued)

OTHER PUBLICATIONS

Badische Anilin & soda-Fabrik AG, Supply of Waste Gas for Ureau Synthesis—using contrlled ammonia to carbon dioxide ratio, 1972, DE 2053358 (A1) English translation, 5 pages.*

(Continued)

*Primary Examiner*—Daniel M Sullivan
*Assistant Examiner*—Yate' K Cutliff
(74) *Attorney, Agent, or Firm*—Nixon & Vanderhye P.C.

(57) ABSTRACT

The invention relates to a method for concentrating an aqueous ammonium carbamate stream, which has been formed in a process for the preparation of urea, has a pressure between 0.20 MPa and 0.9 MPa, a temperature between 35° C. and 95° C., and contains at least 25 wt. % $H_2O$, comprising: a pressure increase step, in which the aqueous ammonium carbamate stream is increased in pressure to a pressure between 1.0 MPa and 7 MPa; a condensation step, in which the aqueous ammonium carbamate stream is contacted with a gas stream, which has been formed in a process for the preparation of melamine and which consists essentially of $NH_3$, $CO_2$ and optionally $H_2O$ and has a lower $H_2O$ content than the aqueous ammonium carbamate stream, the gas stream being absorbed in the aqueous ammonium carbamate stream in such a way that a concentrated ammonium carbamate stream is formed that contains between 15 and 35 wt. % $H_2O$; a discharge step, in which the concentrated ammonium carbamate stream is separated and discharged.

9 Claims, 6 Drawing Sheets

FOREIGN PATENT DOCUMENTS

| | | | |
|---|---|---|---|
| DE | 2 053 358 | | 5/1972 |
| GB | 987500 | * | 3/1965 |
| GB | 1148767 | | 4/1969 |
| WO | WO 02/090232 A1 | | 11/2002 |
| WO | WO 03010089 | * | 2/2003 |
| WO | WO 03/087043 A1 | | 10/2003 |
| WO | WO 2004/011419 A1 | | 2/2004 |
| WO | WO 2005/080321 A1 | | 9/2005 |

OTHER PUBLICATIONS

International Search Report mailed Jul. 27, 2006 in PCT/NL2006/000249.

* cited by examiner

METHOD FOR CONCENTRATING AN AQUEOUS AMMONIUM CARBAMATE STREAM This application is the US national phase of international application PCT/NL2006/000249 filed 15 May 2006 which designated the U.S. and claims benefit of NL 1029038, dated 13 May 2005, the entire content of which is hereby incorporated by reference.

FIELD

The invention relates to a method for utilizing a gas stream, which has been formed in a process for the preparation of melamine and consists essentially of $NH_3$, $CO_2$ and optionally $H_2O$, for the preparation of urea.

BACKGROUND AND SUMMARY

Such a method is disclosed in WO 98/08808 A1. In the known process the gas stream originates from a high-pressure process for the preparation of melamine; the gas stream is supplied directly to a high-pressure section of a stripping process for the preparation of urea.

A disadvantage of the known method is that stable operation of the resulting combined process for the preparation of melamine and urea is difficult: pressure fluctuations in one of the processes can easily affect the other process via the gas stream and thus result in unstable operation. Another disadvantage is that the best operation of the known method is achieved if the melamine process has a higher pressure than said high-pressure section of the urea process.

It is the aim of the invention to reduce or even avoid said disadvantages, while still providing an energy-efficient method of utilizing a gas stream which has been formed in a process for the preparation of melamine.

Said aim is achieved in that the gas stream is used in a method for concentrating an aqueous ammonium carbamate stream. This method for concentrating an aqueous ammonium carbamate stream, which has been formed in a process for the preparation of urea, has a pressure between 0.20 MPa and 0.90 MPa, a temperature between 35° C. and 95° C., and which contains at least 25 wt. % $H_2O$, comprises:

a pressure increase step, in which the aqueous ammonium carbamate stream is increased in pressure to a pressure between 1.0 MPa and 7 MPa;

a condensation step, in which the aqueous ammonium carbamate stream is contacted with a gas stream, which has been formed in a process for the preparation of melamine and consists essentially of $NH_3$, $CO_2$ and optionally $H_2O$ and has a lower $H_2O$ content than the aqueous ammonium carbamate stream, the gas stream being absorbed in the aqueous ammonium carbamate stream in such a way that a concentrated ammonium carbamate stream is formed that contains between 15 and 35 wt. % $H_2O$;

a discharge step, in which the concentrated ammonium carbamate stream is separated and discharged.

The method according to the invention has the advantage that the gas stream originating from a process for the preparation of melamine can be used in an efficient and stable way for the preparation of urea. The increased stability compared to the known method results a.o. from the fact that the raw materials originating in the process for the preparation of melamine are introduced in the high-pressure synthesis section of the urea process in liquid form, not in gaseous form. Yet there is—as a further advantage of the method according to the invention—no need to supply extra water—for example to the gas stream or to the process for the preparation of urea—in order to be able to introduce the gas stream as raw material into a process for the preparation of urea. Yet a further advantage of the method according to the invention is that the pressure of the gas stream from the process for the preparation of melamine does not need to be at least as high as the pressure in the high-pressure section of the urea plant.

DE 14 68 207 A1 discloses a process for the preparation of urea from ammonia vapours that comprise carbon dioxide and possibly water. The ammonia vapours may originate from the synthesis of melamine from urea. The ammonia vapours are directed into a mixing/condensing apparatus where they are mixed with another gaseous water-containing ammonia stream which is a recycling stream created from the effluent from the urea-preparing reactor. After having been mixed, the vapours are condensed. The liquid stream is then fed back into the reactor WO 02/090323 A discloses a process for the preparation of urea from ammonia and carbon dioxide in which a urea synthesis solution containing urea, ammonium carbamate and unconverted ammonia is formed in a synthesis zone, a part of the urea synthesis solution being transferred from the synthesis zone to a medium-pressure treatment zone operating at a pressure of 1-4 MPa, and a gas stream from the medium-pressure treatment zone being absorbed into the low-pressure ammonium carbamate solution from the urea recovery section. WO 02/090323 A does not relate to the use of a gas stream formed in a process for the preparation of melamine.

WO 03/087043 A discloses a process for the preparation of urea from ammonia and carbon dioxide in a urea process wherein the synthesis section contains a scrubber wherein the off-gas stream from the synthesis section is purified of ammonia and carbon dioxide and wherein the scrubber is a medium-pressure scrubber that is operated at a pressure of 1-5 MPa. WO 03/087043 A also relates to a process for modifying existing urea processes and a urea plant comprising a high-pressure synthesis section wherein a medium-pressure scrubber is included. WO 03/087043 A does not relate to the use of a gas stream formed in a process for the preparation of melamine.

WO 2004/011419 A discloses a process for increasing the capacity of a urea plant comprising a compression section, a high-pressure synthesis section, a urea recovery section, in which a urea melt is formed, and optionally a granulation section, the capacity of the urea plant being increased by the additional installation of a melamine plant and the urea melt from the urea recovery section of the urea plant being fed wholly or partly to the melamine plant and the residual gases from the melamine plant being returned wholly or partly to the high-pressure synthesis section and/or the urea recovery section of the urea plant.

DE 20 53 358 A1 discloses a process for the feeding of carbon dioxide-containing gases, e.g. off-gases generated in the synthesis of melamine from urea, into a plant for the preparation of urea. The plant for preparing urea contains a high-pressure section and a recycle section for the recovery of non-converted ammonia and carbond dioxide having a low-pressure and a medium-pressure section. An ammonium carbamate solution as recycle stream is generated in a low-pressure section at a pressure between 0.1 MPa and 0.4 MPa, then increased in pressure in a medium-pressure section to between 1 and 3 MPa. From the medium-pressure section the recycle stream is again increased in pressure to between 1.5 and 6 MPa and fed to an absorption zone that is placed before the high-pressure section. To the absorption section are also fed the carbon dioxide-containing gases, e.g. off-gases generated in the synthesis of melamine from urea GB 1 148 767 A discloses a process for the synthesis of melamine which consists of an aqueous carbon dioxide-ammonia system for producing urea operating at 180-200° C.

and 180-220 kg/cm$^2$, the product being depressurized to 40-60 kg/cm$^2$, and a urea-ammonia system for producing melamine operating at 360-450° C. and 60-150 kg/cm$^2$, the melamine waste gas, a by-product of the latter system, being utilized for urea synthesis in the former system and the urea obtained from the former system being circulated to the latter system for melamine synthesis, wherein the waste gas (comprising ammonia and carbon dioxide) which is discharged from the top of the melamine reaction vessel is introduced directly into a waste gas absorption cell operated at 130-160° C. and 60-150 kg/cm$^2$ in the recycle circuit of aqueous ammonium carb-amate in the urea-producing system, the resulting concentrated aqueous ammonium carbamate being used for urea synthesis in the urea-producing system; the sensible heat of the waste gas and the heat of ammonium carbamate formation being utilized for decomposition of unreacted ammonium carbamate and generation of steam; excess ammonia being recovered as liquid ammonia in the waste gas cell.

WO 2005/080321 A, published on 01.09.2005, discloses an integrated process for urea and melamine production. Urea is produced in a urea plant comprising a high pressure urea synthesis section and a urea recovery section for separating urea from a carbamate aqueous solution, and melamine is produced in a melamine plant wherein off-gases resulting as byproducts of the melamine synthesis are discharged therefrom at a pressure of at least 2 bar and recycled to the high pressure urea synthesis section.

The method according to the invention relates to the concentrating of an aqueous ammonium carbamate stream. Concentrating is here understood to mean that the $H_2O$ content, expressed in percents by weight, decreases. As meant herein, concentrating is primarily achieved by preferential addition of compounds other than $H_2O$ to the aqueous ammonium carbamate stream rather than by withdrawing $H_2O$ from the aqueous ammonium carbamate stream. The method according to the invention is preferably operated in such a way, as explained below, that the $H_2O$ content of the aqueous ammonium carbamate stream decreases by at least 3 wt. %, relative to the aqueous ammonium carbamate stream as a whole. More preferably the $H_2O$ content decreases by at least 5 wt. %, even more preferably by at least 8 wt. % or even 10 wt. %, and most preferably by at least 15 wt. %. In view of the practical restrictions arising from, among other things, the desire, as explained later, to avoid solids formation, it is preferred for the $H_2O$ content of the aqueous ammonium carbamate stream to decrease by at most 30 wt. %, more preferably by at most 25 wt. %.

An aqueous ammonium carbamate stream is here understood to be a substantially liquid stream in which water is the continuous phase and which contains ammonium carbamate—either as such in dissolved form or in solid form, or in the form of free $NH_3$ and/or free $CO_2$.

According to the invention the aqueous ammonium carbamate stream has been formed in a process for the preparation of urea. In principle, any type of process for the preparation of urea on the basis of $NH_3$ and $CO_2$ is suitable for this. Examples of such processes, which are known in themselves, are the processes as mentioned in chapter 3, 'Production', of the urea section of Ullmann's Encyclopaedia of Industrial Chemistry, Wiley-VCH Verlag GmbH & Co, 1996 or the electronic version thereof, DOI: 10.1002/14356007.a27_333, online posting date Jun. 15, 2000. In particular both the so-called conventional processes, as described in chapter 3.3.1 of said encyclopaedia, and the so-called stripping processes, as described in chapter 3.3.2, are suitable.

Stripping processes as understood by the skilled person and as contemplated herein are based on the principle that ammonium carbamate as present in the effluent of the urea synthesizing reactor can be induced to decompose into $NH_3$ and $CO_2$ to a large extent at a high overall pressure if it is ensured that the partial pressure of either $CO_2$ or $NH_3$ is lowered. In a $CO_2$ stripping process a lowering of the partial pressure of $NH_3$ is achieved through the introduction of $CO_2$ into the effluent of the reactor. In an $NH_3$-stripping process the already present excess of $NH_3$ and/or the introduction of extra $NH_3$ into the effluent of the reactor results in the decomposition of ammonium carbamate as a consequence of the low or lowered $CO_2$ partial pressure.

A characteristic of the stripping process as done in a stripping plant is thus that a stripping action is done—typically in a stripper—on the effluent of the reactor, assisted with or even fully based on the input of heat energy. In a $CO_2$ stripping process, $CO_2$ is added to the stripper and this accounts for the majority, or even for 75%, 90% or even all of the fresh $CO_2$ that is consumed. Fresh $CO_2$ means $CO_2$ that is introduced as separate raw material stream, with no or virtually no $NH_3$ in it.

A further characteristic of a stripping processes as done in a stripping plant is that the pressure at which stripping takes place lies between 11 MPa and 20 MPa, preferably between 12.5 and 19 MPa. Preferably and typically the pressure at which the stripping action is carried out is substantially equal to the pressure in the reactor. Substantially equal means that the pressure in the stripper is less than 0.5 MPa higher or lower than in the reactor, and that in a stripping plant wherein a stripping process is executed no pressure-reducing means such as a valve are present between reactor and stripper.

The reactor and the stripper are core components of the so-called high-pressure section for the execution of a urea stripping process in a urea stripping plant. Usually and preferably, the condenser—in which the gaseous stream exiting the stripper is condensed so as to feed it to the reactor—is also part of the said high-pressure section. The condenser may be integrated with the reactor itself.

An effect of the stripping action in a stripping process is that the gaseous stream so generated comprises a significant portion of the raw materials not converted into urea. This is usually at least 25 wt. % of the total of the raw materials not converted into urea that are being fed back to the reactor; preferably, at least 40, 50, 60, or even at least 70 wt. % of the raw materials not converted into urea are being recycled back to the reactor within the high-pressure section via the stripper and the condenser.

A further effect of the stripping action according to the principle of the stripping process is that the gaseous stream leaving the stripper contains a relatively low percentage of $H_2O$; typically less than 10 wt. %, or even less than 8, 6, 5 or even 4 wt. % of $H_2O$.

In all such processes for the preparation of urea, as is known and including conventional processes as well as stripping processes, aqueous ammonium carbamate streams are formed with a pressure between 0.20 MPa and 0.90 MPa—or between 0.20 MPa and 0.60 MPa—and containing at least 25 wt. % water; this holds in particular in those parts of the process—and of the plant wherein the process is executed—where the unreacted raw materials are separated from the formed urea and are returned directly or indirectly to the synthesis section. The said parts comprise a low-pressure section. With low pressure is meant herein a pressure between about atmospheric and 1 MPa. The said parts may also comprise a medium-pressure section. With medium pressure is meant herein a pressure between 1 MPa and 10 MPa. Plants for the preparation of urea also contain a high-pressure section. With high pressure is meant herein a pressure between 10 MPa and about 30 MPa or in a narrower range falling within 10 MPa and 30 MPa, which is indicated herein where applicable.

Within the context of the present invention the terms high pressure and low pressure are also used in relation to processes for the preparation of melamine; there, these terms have a different meaning as elucidated there.

Prior to the execution of the pressure increase step the pressure of the aqueous ammonium carbamate stream preferably is or is brought to between 0.20 and 0.80 MPa, between 0.20 MPa and 0.60 MPa, between 0.25 and 0.60 MPa or between 0.25 MPa and 0.55 MPa, more preferably between 0.30 MPa and 0.50 MPa. The temperature of the aqueous ammonium carbamate stream lies between 35° C. and 95° C. or between 50° C. and 95° C.; preferably the temperature lies between 60° C. and 90° C., more preferably between 65° C. and 85° C. If the aqueous ammonium carbamate stream as formed in the low-pressure section of a plant for the preparation of urea does not have a temperature lying in a desired range according to the invention, a preheating step or a precooling step, carried out prior to or during the pressure increase step, should be implemented so as to assure that the temperature of the aqueous ammonium carbamate stream is brought to within the desired range. The $H_2O$ content of the aqueous ammonium carbamate stream is at least 25 wt. % or 30 wt. %; this content is desirable in practice to prevent significant formation of solid particles occurring at said pressures between 0.20 MPa and 0.90 MPa. Said solid particles usually consist of ammonium carbamate. In view of the general aim in processes for the preparation of urea to limit the amount of water in ammonium carbamate streams, especially when those streams are supplied directly or indirectly via intermediate operations to a urea synthesis section, the aqueous ammonium carbamate stream will usually not contain more than 60 wt. % $H_2O$, preferably less than 50 wt. %.

The molar $NH_3/CO_2$ ratio of the aqueous ammonium carbamate stream, which, as is known, is calculated by also converting all $NH_3$- and $CO_2$-derived compounds such as ammonium carbamate into molar $NH_3$ and $CO_2$ equivalents and including these in the count, typically and also preferably lies between 1 and 5 or 4; more preferably said ratio lies between 1.5 and 3 or 2.5.

The method according to the invention comprises a pressure increase step, in which of the aqueous ammonium carbamate stream is increased in pressure to a pressure between 1 MPa and 7 MPa. The pressure increase can be effected in any suitable way, such as for example with the aid of a pump; such methods are in themselves known to one skilled in the art, as is the condition that the corrosive character of an aqueous ammonium carbamate stream is to be taken into account. The amount of water in an aqueous ammonium carbamate stream that is at least needed to prevent ammonium carbamate from crystallizing out depends a.o. on the pressure: the higher the pressure, the lower the minimum amount of water needed. As is known, a further important factor that influences the presence or formation of solid ammonium carbamate is the temperature.

As a consequence of the pressure increase step it is therefore possible to reduce the $H_2O$ content of the aqueous ammonium carbamate stream without the presence of—or an increase in—crystallized ammonium carbamate. Preferably the pressure is increased to between 1 MPa and 7 MPa in the pressure increase step; more preferably the pressure is increased to between 1.5 and 6 or 5 MPa in the pressure increase step, most preferably to between 2 and 4.5 or 4 MPa.

The increase of pressure in the pressure increase step is preferably at least 0.5 or 1 MPa, more preferably at lease 1.5 MPa or 2 MPa. A higher increase of the pressure has the advantage that the aqueous ammonium carbamate stream can be concentrated to a larger extent without the formation of solid particles such as crystallized ammonium carbamate particles. The increase of pressure should not be so high as to raise the pressure to a value higher than 7 MPa.

In the method according to the invention the pressure increase step is followed by a condensation step. In this step the aqueous ammonium carbamate stream is contacted with a gas stream. The gas stream has been formed in a process for the preparation of melamine; this is understood to mean that the gas stream is formed in a process for the preparation of melamine and contains by-products that are formed directly or indirectly in the synthesis of melamine from urea. As is known, these by-products are mainly $NH_3$ and $CO_2$. In principle, the gas stream can be formed in any process for the preparation of melamine from urea, such as the processes disclosed in Ullmann's Encyclopedia of Industrial Chemistry, Electronic edition, chapter Melamine and Guanamines, Wiley-VCH Verlag GmbH & Co, DOI: 10.1002/14356007.a16_171, Article Online Posting Date: Mar. 15, 2001. Examples of such processes are the so-called non-catalytic, high-pressure liquid-phase processes, in which molten urea is converted into liquid melamine at a pressure between 5 and 25 MPa and a temperature between 325° C. and 450° C. without the aid of a catalyst, and the so-called catalytic, low-pressure gas-phase processes, in which urea is converted into gaseous melamine at a pressure between atmospheric and 1, 2 or 3 MPa and with the aid of a catalyst.

An example of the formation of the gas stream is the separation, known in itself, of gaseous products from liquid melamine in a reactor in a liquid-phase process or in a gas/liquid separation apparatus installed downstream of the reactor. If desired, the gas stream can be passed through the liquid urea that is fed to the process before being used in the method according to the invention. The gas stream then consists essentially of $NH_3$ and $CO_2$. The terms 'consist essentially of' and equivalents thereof have the usual meaning that should other compounds are present or should other measures are taken then these are such that they do not have a significant influence on the working or effects of the invention.

Another example of the formation of the gas stream is by means of the separation, known in itself, of gaseous products that are formed upon the cooling by means of an aqueous stream of the gaseous reaction mixture formed in a low pressure gas-phase process for the preparation of melamine. The gas stream thus formed contains $H_2O$ besides $NH_3$ and $CO_2$.

In one embodiment of the invention the gas stream is separated from a so-called desorber; this is a column known in itself which is fed with an aqueous ammonium carbamate stream that is formed in a low-pressure gas-phase process for the preparation of melamine and from which a gas stream is released that is—as a result of its composition, in particular relating to $H_2O$ content—suitable for use as gas stream in the method according to the invention.

The gas stream consists essentially of $NH_3$, $CO_2$ and optionally $H_2O$. As indicated above, the presence and amount of $H_2O$ is normally determined by the embodiment of the melamine process in which the gas stream has been formed. The $NH_3$ and $CO_2$ in the gas stream may have been formed as by-product in the melamine process, but can also, as is known in itself, have been supplied to it as auxiliary material. In addition, the gas stream may contain up to 10 wt. % of other compounds; examples are urea or melamine. Preferably, the gas stream contains less than 7, more preferably less than 5 wt. % or even essentially 0 wt. % of other compounds.

The gas stream is contacted with the aqueous ammonium carbamate stream in the condensation step to be discussed below, the aim being to concentrate the aqueous ammonium carbamate stream. It follows that the gas stream should contain less water than the aqueous ammonium carbamate stream. Preferably the water content of the gas stream is at least 10 wt. % lower than that of the aqueous ammonium carbamate stream, more preferably at least 20 wt. % lower, the weight percentages being related to the streams as a whole. This has the advantage that stronger concentration of the aqueous ammonium carbamate stream is possible. Preferably the gas stream contains less than 40 wt. % water; in a preferred embodiment of the invention the gas stream contains less than 15 wt. %, or even less than 10 wt. %, less than 5 wt. % or practically no water.

The gas stream has been formed in a process for the preparation of melamine; preferably and if possible the pressure and temperature of the gas stream are not changed at the start of the condensation step to be discussed below. Preferably the pressure increase step is carried out in such a way that the gas stream can directly, without further pressure changes—and in particular without a pressure increase—be contacted with the aqueous ammonium carbamate stream. In an alternative embodiment of the invention, however, the gas stream is condensed separately and at least partially so as to form an intermediate ammonium carbamate stream. The intermediate ammonium carbamate stream may be essentially anhydrous and as such be comparable to the ammonium carbamate stream as disclosed in WO 98/32731 A page 3 lines 9-14 and page 4 lines 20-36. The intermediate ammonium carbamate stream may also be aqueous; it may be a liquid or a gas/liquid mixture. In this embodiment of the invention, instead of the gas stream the intermediate ammonium carbamate stream is fed to the condensation step. Also in this alternative embodiment, most if not all of the heat released in the formation of ammonium carbamate is already released in the formation of the intermediate ammonium carbamate stream; this heat maybe recovered by means as such known.

During the condensation step the aqueous ammonium carbamate stream and the gas stream are contacted with each other in order to achieve full or at least partial absorption in the aqueous ammonium carbamate stream of the $NH_3$ and $CO_2$ in the gas stream. Contacting can take place using methods known in themselves, for example by condensing the gas stream in a condenser, with the released condensation heat being dissipated in cooling water, the aqueous ammonium carbamate stream also being supplied to the condenser such that the gas stream is absorbed—as such or in condensed form. Contacting can for example also take place in a column to which the two streams are supplied and where they are contacted cocurrently or countercurrently. Such a column can be designed with the gas stream as the continuous phase, but also with the aqueous ammonium carbamate stream as the continuous phase. As is known, a packing can be used to promote the contact between the two streams. Contacting can also take place using a combination of said condenser and column.

During absorption of the gas stream in the aqueous ammonium carbamate stream, heat is released as a result of the formation of ammonium carbamate from $NH_3$ and $CO_2$. It is therefore, as indicated above, advantageous to provide for heat discharge during the condensation step. This can be done by means of techniques known in themselves, such as a heat exchanger, which can then for example be used for steam generation purposes.

As a result of either the absorption of the gas stream in the aqueous ammonium carbamate stream or the combining of the intermediate ammonium carbamate stream with the aqueous ammonium carbamate stream a concentrated ammonium carbamate stream is formed. It is important that any formation of ammonium carbamate in solid form be controlled and avoided, since it is disadvantageous is to have a too large amount of solids in the concentrated ammonium carbamate. As indicated before, and as is known, the amount of ammonium carbamate that can be dissolved in water is dependent on the pressure. The amount of gas stream to be absorbed therefore preferably is such that the concentrated ammonium carbamate stream at the prevailing pressure contains less than 10 or 8 wt. % ammonium carbamate in solid form, preferably less than 6, 5 or 4 wt. %, and most preferably 3, 2, 1 wt. % ammonium carbamate in solid form or virtually none or even none at all. Preferably a heat exchange is applied during the condensation step, such that the concentrated ammonium carbamate stream formed has a temperature between 75° C. and 160° C. or between 80° C. and 140° C., more preferably between 85° C. and 130° C. or between 90° C. and 120° C., most preferably between 95° C. and 110° C. The heat exchange may be implemented by means as such known, such as a heat exchanger. In order to achieve temperatures of the concentrated ammonium carbamate stream as indicated upon formation, it may be necessary to implement the heat exchange in such a way as to cool the aqueous ammonium carbamate stream as it is being concentrated; however, it was found that it is at the same time important to avoid that the temperature of the aqueous ammonium carbamate stream as it is being concentrated does not drop too low—even locally—in view of the danger of precipitation of solids. It is preferred, therefore, that the temperature of the cooling medium that is used for the heat exchange action lies between 40 and 110° C., preferably between 70 and 100° C. These relatively high temperature of the cooling medium—which cooling medium is preferably water—implies, as the skilled person knows and as follows from routine calculations, that the heat exchange surface may need to be relatively large. It may even mean that during a part of the condensation step the cooling medium is actually increasing the temperature of the concentrated ammonium carbamate stream in formation.

The molar N/C ratio of the gas stream formed in a process for the preparation of melamine may be different from the N/C ratio of the aqueous ammonium carbamate stream. In such a case, the N/C ratio of the concentrated ammonium carbamate stream would also deviate from that of the aqueous ammonium carbamate stream; this deviation could bring the N/C ratio outside of the range that is desirable for the subsequent preparation of urea. If that is the case it is preferred to introduce additional $NH_3$ or $CO_2$ such that the N/C ratio is within the desired range within the urea-synthesizing reactor. The introduction of additional $NH_3$ or $CO_2$ could take the form of combining this with the concentrated ammonium carbamate stream during or subsequent to the condensation step; however, it could also take the form of a direct feed to the reactor or any other stream fed to the reactor. In a preferred embodiment, the molar N/C ratio of the concentrated ammonium carbamate is brought to between 2.0 and 3.0, preferably between 2.3 and 2.6; preferably this is done through the injection of additional $NH_3$ or $CO_2$.

After the condensation step in the method according to the invention the concentrated ammonium carbamate stream is, if necessary and has not already done so by itself, separated from the gas stream and the aqueous ammonium carbamate stream, and discharged.

In one embodiment of the invention the concentrated ammonium carbamate stream is used for the synthesis of urea. Preferably the concentrated ammonium carbamate stream is increased in pressure to between 12.5 and 20 MPa or between 13 and 19 MPa and supplied to a high-pressure section of a stripping process for the preparation of urea, which is generally also operated at a pressure between 12.5 and 20 MPa. Preferably the concentrated ammonium carbamate stream is increased to such a pressure that the stream can directly and without further pressure adjustments be supplied to a high-pressure section of a stripping process. Such a high-pressure section, which is known in itself, comprises at least a reactor, a stripper and preferably also a condenser. The concentrated ammonium carbamate is preferably supplied to the condenser or the reactor in the said high-pressure section, directly or via an intermediate line or apparatus. The stripping process for the preparation of urea is preferably a so-called $CO_2$ stripping process, an $NH_3$ or self-stripping process, or an ACES stripping process. Said processes are known in themselves, as referred to earlier in the description of the present invention or in for example the chapters 3.3.2.1, 3.3.2.2 and 3.3.2.3 of the previously mentioned urea section of Ullmann's Encyclopaedia of Industrial Chemistry.

In a preferred embodiment of the invention the stripping process is a $CO_2$ stripping process for the preparation of urea. The present invention is especially advantageous for those plants for executing a $CO_2$ stripping process that do not have a medium-pressure section, which means a section that is operated at a pressure between about 1 MPa and about 10 MPa, so that an aqueous ammonium carbamate stream that has been formed in the low-pressure section, which means at a pressure between about atmospheric and about 1 MPa, and that in the known method is supplied directly to the high-pressure section, can be concentrated by means of the method according to the invention, so that relatively less water is supplied to the urea synthesis reactor, as a result of which the synthesis reactor can operate with a higher efficiency. The implementation of the present invention in a $CO_2$ stripping process that does not have process steps executed at medium-pressure—or in any other process for the preparation of urea that does not have process steps executed at medium-pressure—thus amounts to the introduction of a series of medium-pressure steps, namely at least the pressure increase step, condensation step and discharge step according to the invention.

If the method according to the invention is implemented in a $CO_2$ stripping process for the preparation of urea, then it is preferred to consider the ratio of the $CO_2$ as introduced from the process for the preparation of melamine ($C_M$) and the fresh $CO_2$ that is used as stripping agent ($C_S$). It is preferred that the molar $C_M/C_S$ ratio is at most 3, more preferably at most 2 or 1, most preferably at most 0.5 or 0.25. The said ratio is preferably at least 0.05 or 0.1. Although it is an advantage of the method according to the invention that the danger of interfering negatively with the efficiency of the stripping action is reduced compared to the case where a $NH_3$— and $CO_2$ containing stream from the process from the preparation of melamine is fed directly to the high-pressure section of the urea plant, it is still preferred that a significant amount of fresh $CO_2$ remains available so that the stripping action may be carried out satisfactorily.

By analogy, if the method according to the invention is implemented in a $NH_3$ stripping process for the preparation of urea, then it is preferred to consider the ratio of the $NH_3$ as introduced from the process for the preparation of melamine ($N_M$) and the fresh $NH_3$ that is introduced into the stripping process ($N_S$). It is preferred that the molar $N_M/N_S$ ratio is at most 3, more preferably at most 2 or 1, most preferably at most 0.5 or 0.25. The molar $N_M/N_S$ ratio is preferably at least 0.05 or 0.1.

The method according to the invention can therefore be used to increase the stability and/or capacity of a plant for the synthesis of urea. This may be achieved by making a plant for the synthesis of urea suitable for executing the process of the present invention. Such a plant according the invention comprises a high-pressure synthesis section, which means a section that is operated at a pressure between about 10 MPa and about 30 MPa or in a narrower range between 10 MPa and 30 MPa, which is indicated herein where applicable. Such a plant according the invention also comprises a low-pressure recirculation section, and further means for supplying an aqueous ammonium carbamate stream that has been formed in the low-pressure recirculation section to the high-pressure synthesis section. If the plant does not comprise means for increasing the aqueous ammonium carbamate stream in pressure to between 1 MPa and 7 MPa, then such means are to be additionally installed in the method according to the invention. Further, according to the method of the invention means are additionally installed for contacting the aqueous ammonium carbamate stream at a pressure between 1.0 MPa and 7 MPa with a gas stream or a gas/liquid stream or a liquid stream, which has been formed in a process for the preparation of melamine and consists essentially of $NH_3$, $CO_2$ and optionally $H_2O$, the additionally installed means being such that the gas stream is at least partly but preferably wholly absorbed in the aqueous ammonium carbamate stream so that a concentrated ammonium carbamate stream can be formed. In order to accommodate for the increased capacity of the plant for the synthesis of urea, it may be preferable or even necessary that one or more other apparatuses are increased in capacity; this may in particular be the case where previously no $NH_3$- and $CO_2$-containing stream as formed in a process for the preparation of melamine had been introduced as raw material into the plant for the synthesis of urea. Examples of apparatuses that may need to be increased in capacity in a urea stripping plant include the reactore and/or stripper and/or the condenser in the high-pressure section.

Preferably the additionally installed means according to the method of the invention comprise process control means enabling the amount of gas stream to be absorbed to be set in such a way that the concentrated ammonium carbamate stream contains between 15 and 35 wt. % $H_2O$. The concentrated ammonium carbamate stream is then supplied to the high-pressure synthesis section—wholly or partly replacing the aqueous ammonium carbamate stream. The plant for the preparation of urea can be a conventional plant; preferably the plant for the preparation of urea is a stripping plant, which means a plant that is suitable for operating the stripping process wherein the high-pressure section of the stripping plant comprises a reactor and a stripper, whereby the effluent of the reactor is treated in the stripper with heat and/or with $CO_2$ and whereby no pressure-reducing apparatus is present between the reactor and the stripper. Preferably the plant to be adapted does not have a section comprising an absorber or condenser operating at a pressure between 1 MPa and 10 MPa.

Closely associated with the above-mentioned method for increasing the capacity of a plant for the synthesis of urea, the invention also relates to a plant for the synthesis of urea, the plant comprising a high-pressure synthesis section and a low-pressure recirculation section, with the plant comprising means for supplying an aqueous ammonium carbamate stream formed in the low-pressure recirculation section to the high-pressure synthesis section. The plant according to the invention comprises means for increasing the aqueous ammonium carbamate stream in pressure to between 1 MPa and 7 MPa; further the plant according to the invention comprises means for contacting the aqueous ammonium carbamate stream at a pressure between 1 MPa and 7 MPa with a gas stream or a gas/liquid stream or a liquid stream formed in a process for the preparation of melamine and consisting essentially of $NH_3$, $CO_2$ and optionally $H_2O$, the means being such that the gas stream is absorbed in the aqueous ammonium carbamate stream so that a concentrated ammonium carbamate stream can be formed. Preferably the plant comprises means for setting the amount of gas stream to be absorbed such that the concentrated ammonium carbamate stream contains between 15 and 35 wt. % $H_2O$. The concentrated ammonium carbamate stream is then supplied to the high-pressure synthesis section—wholly or partly replacing the aqueous ammonium carbamate stream. The plant for the preparation of urea can be a conventional plant; preferably the plant for the preparation of urea is a stripping plant, which means a plant that is suitable for operating the stripping process.

BRIEF DESCRIPTION OF THE DRAWINGS

Some embodiments of the method according to the invention will be elucidated with reference to the drawings.

In the drawings.

DETAILED DESCRIPTION

The first digit of the numbers in the figures is the same as the number of the figure. If the last two digits of the numbers of different figures agree, they refer to the same element.

Figure 1:
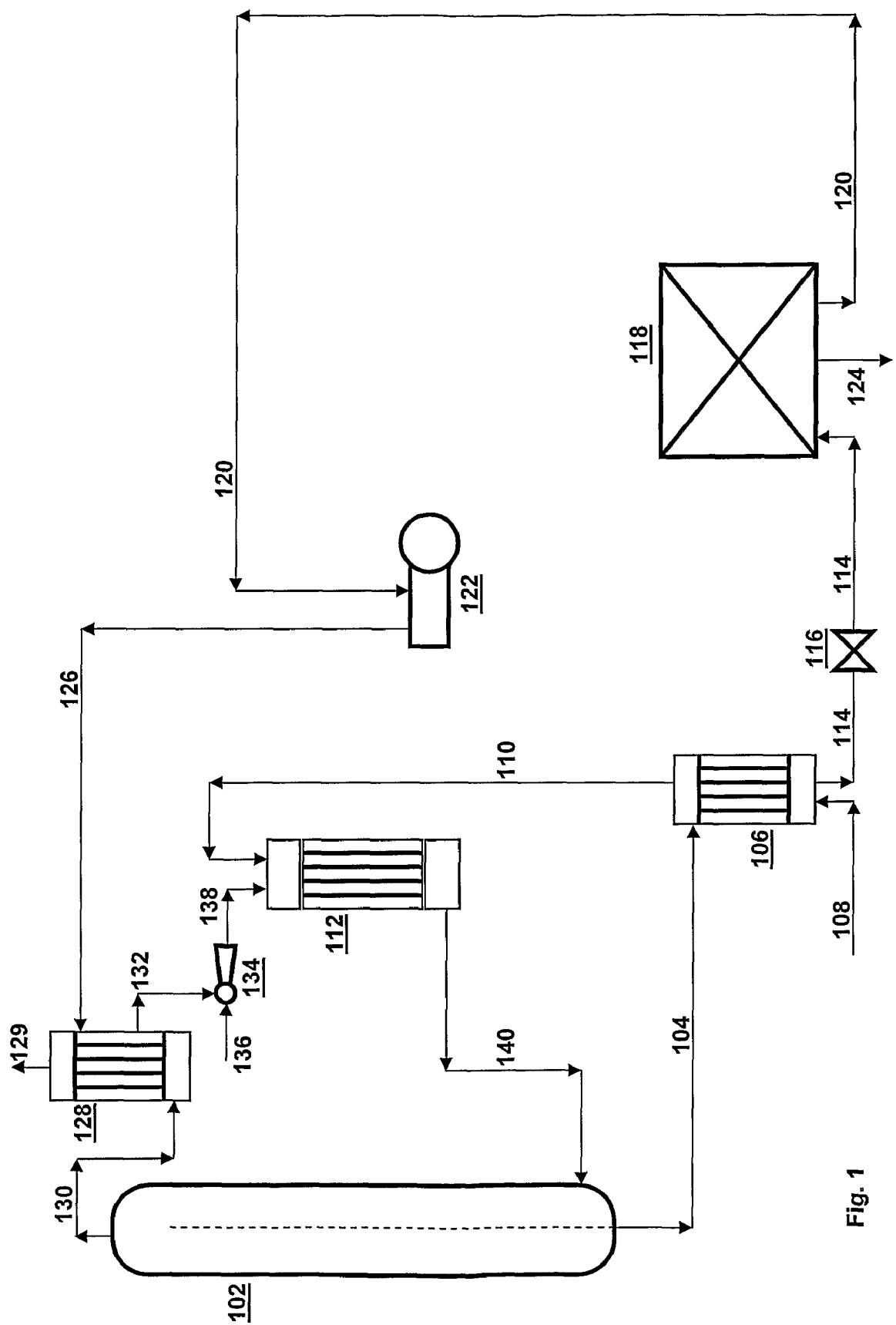
FIG. 1 shows an embodiment of a stripping plant for the preparation of urea according to the state of the art that does not use a gas stream originating from a process for the preparation of melamine.

In FIG. 1 urea is prepared in synthesis column 102 at a synthesis pressure of about 14 MPa. The effluent, the synthesis solution, is supplied via line 104 to high-pressure stripper 106, where the synthesis solution is stripped with $CO_2$, supplied via line 108, so that a large part of the unreacted raw materials is separated in vapour form from the synthesis solution and supplied via line 110 to high-pressure condenser 112. The synthesis effluent is discharged via line 114, reduced in pressure to about 0.4 MPa by means of valve 116 and supplied to the low-pressure recirculation section 118. Here, the remaining unreacted raw materials are recovered in a way known in itself in the form of an aqueous ammonium carbamate stream, which is supplied to compressor 122 via line 120. From the low-pressure recirculation section also the urea itself is recovered, in the form of an aqueous solution that is discharged via line 124. The aqueous ammonium carbamate solution is increased in pressure to synthesis pressure in compressor 122, and then supplied via line 126 to scrubber 128, where off-gases from synthesis column 102, which are supplied via line 130, are absorbed to the maximum extent possible. Any remaining gases such as inerts are discharged through line 129. The aqueous ammonium carbamate solution is next sucked, via line 132, into ejector 134, which is driven by $NH_3$-supplied via line 136. The stream leaving the ejector is supplied via line 138 to high-pressure condenser 112, to be condensed together with the gaseous stream supplied from stripper 106 to yield a stream of raw materials that is supplied via line 140 to synthesis column 102. Synthesis column 102, stripper 106, condenser 112 and scrubber 128 are part of the high-pressure section of the plant.

Figure 2:
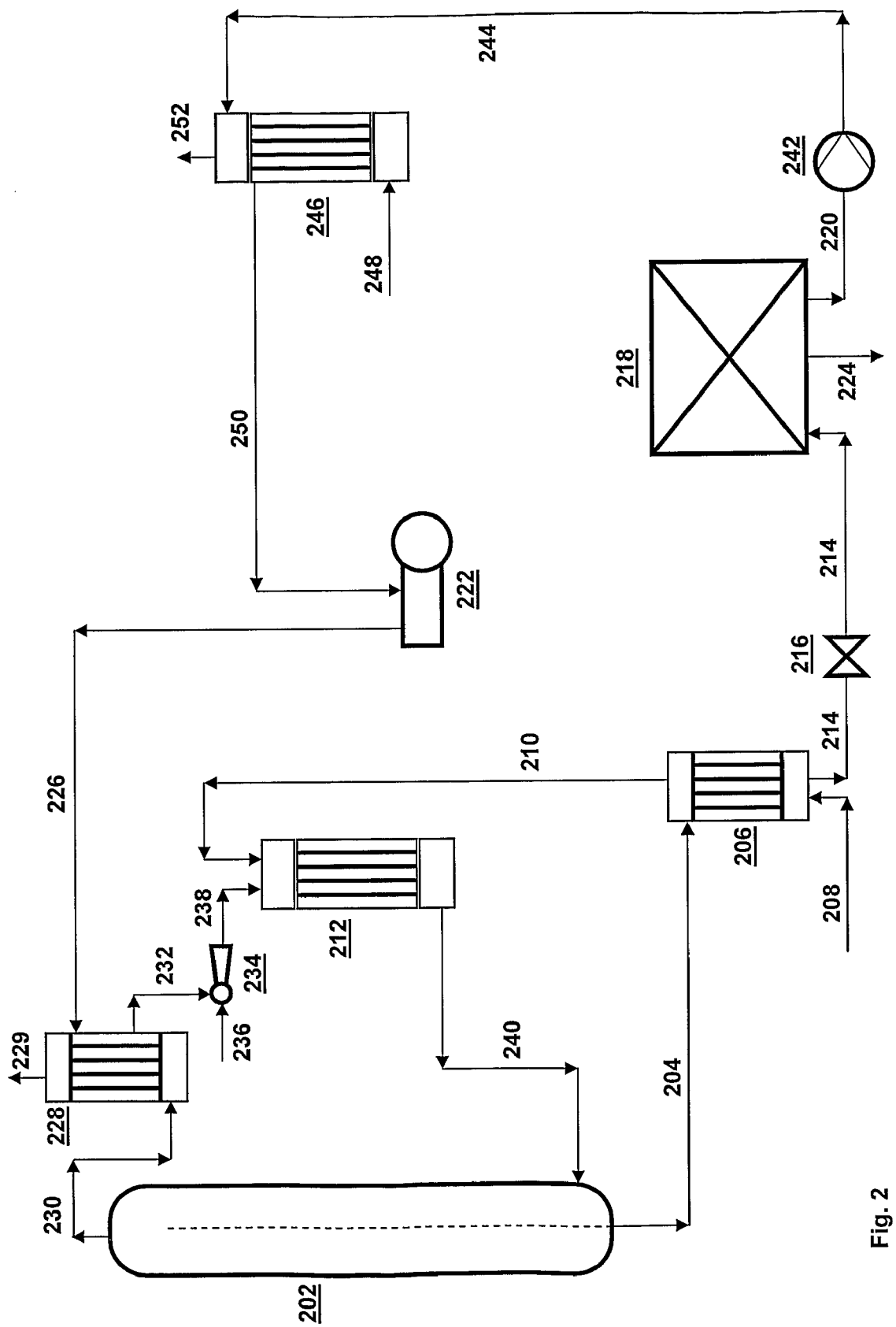
FIG. 2 shows an embodiment according to the invention in which a gas stream, originating from a non-catalytic, high-pressure process for the preparation of melamine, is absorbed in an aqueous ammonium carbamate stream.

In FIG. 2 a plant and method according to the invention is elucidated. In comparison with the situation as represented in FIG. 1 now the aqueous ammonium carbamate stream released via line 220 from the low-pressure recirculation section 218 is first increased in pressure to about 2 MPa by means of pump 242, and next supplied via line 244 to a condenser 246. Via line 248 a gas stream is supplied to condenser 246 that originates from a high-pressure, non-catalytic process for the preparation of melamine. The gas stream consists essentially of $NH_3$ and $CO_2$ and has been given a pressure of 2 MPa. In condenser 246 the gas stream is absorbed in the aqueous ammonium carbamate stream, and the concentrated ammonium carbamate stream is formed. The concentrated ammonium carbamate stream is discharged via line 250, and passed to compressor 222 to be increased in pressure to synthesis pressure. Any gases not absorbed in condenser 246 are discharged via line 252.

Figure 3:
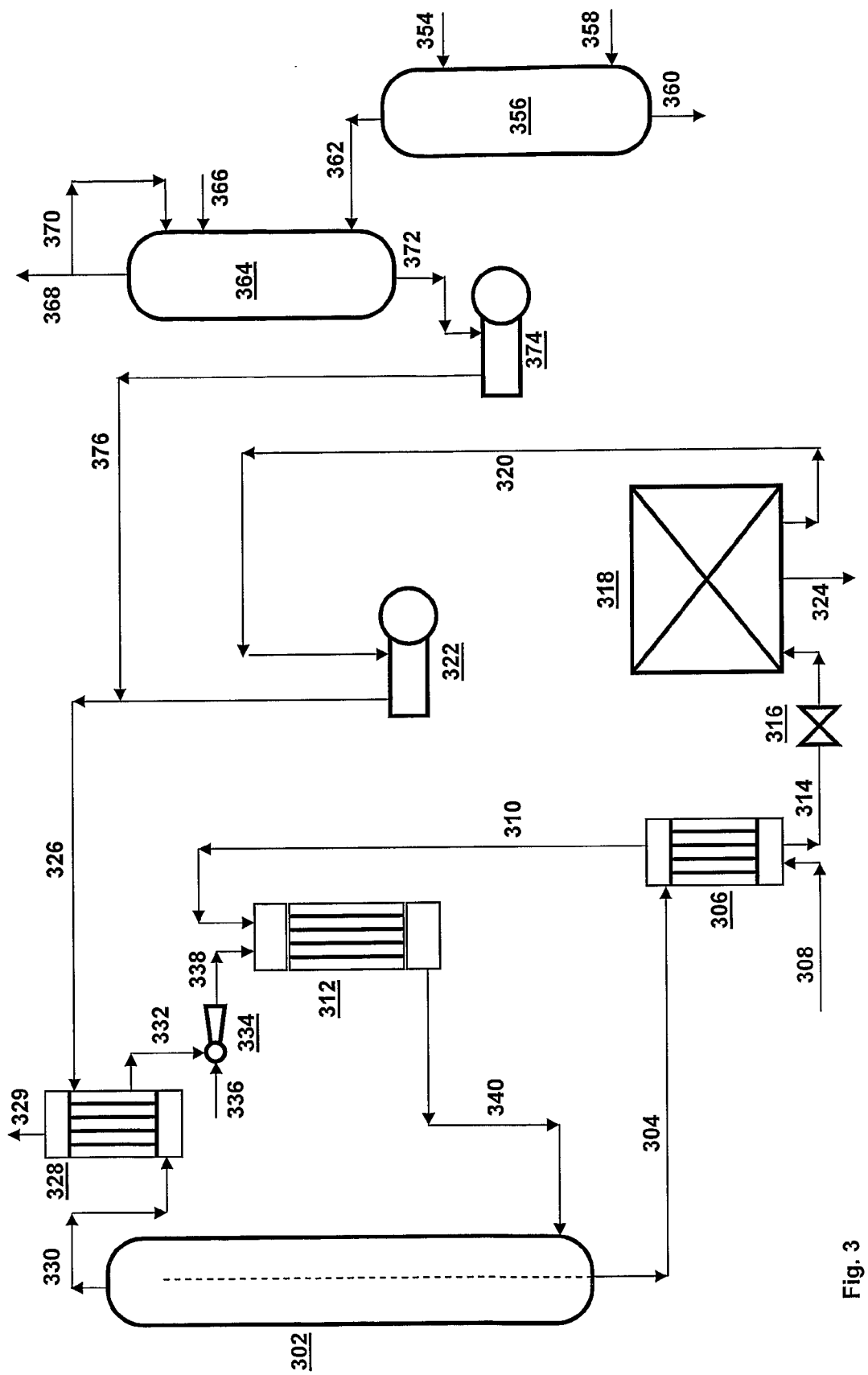
FIG. 3 shows an embodiment according to the state of the art in which a gas stream, originating from a low-pressure, catalytic process for the preparation of melamine, is treated in a concentrating section before being supplied as an aqueous ammonium carbamate stream to a stripping plant for the preparation of melamine.

In FIG. 3 an aqueous ammonium carbamate stream that originates from a low-pressure, non-catalytic process for the preparation of melamine and that contains 40 to 50 wt. % $H_2O$ and has a pressure of about 2 MPa is supplied to desorber 356 via line 354. Desorber 356 is also supplied, via line 358, with steam. The bottom stream from desorber 356 consists essentially of $H_2O$ and is discharged via line 360. From the top of desorber 356 a gas stream is discharged that consists essentially of $NH_3$, $CO_2$ and $H_2O$ and that is fed to absorber 364 via line 362. In addition, water is fed to absorber 364 via line 366, in order to prevent crystallization. The top stream from absorber 364 consists essentially of $NH_3$, which is discharged via line 368 and partly recycled—possibly after having been cooled or partly or wholly condensed—via line 370. The bottom stream from absorber 364 is an aqueous ammonium carbamate stream that is discharged via line 372 to compressor 374 to be increased in pressure to about the urea synthesis pressure, so that the aqueous ammonium carbamate stream can be combined via line 376 with the aqueous ammonium carbamate stream in line 326.

Figure 4:
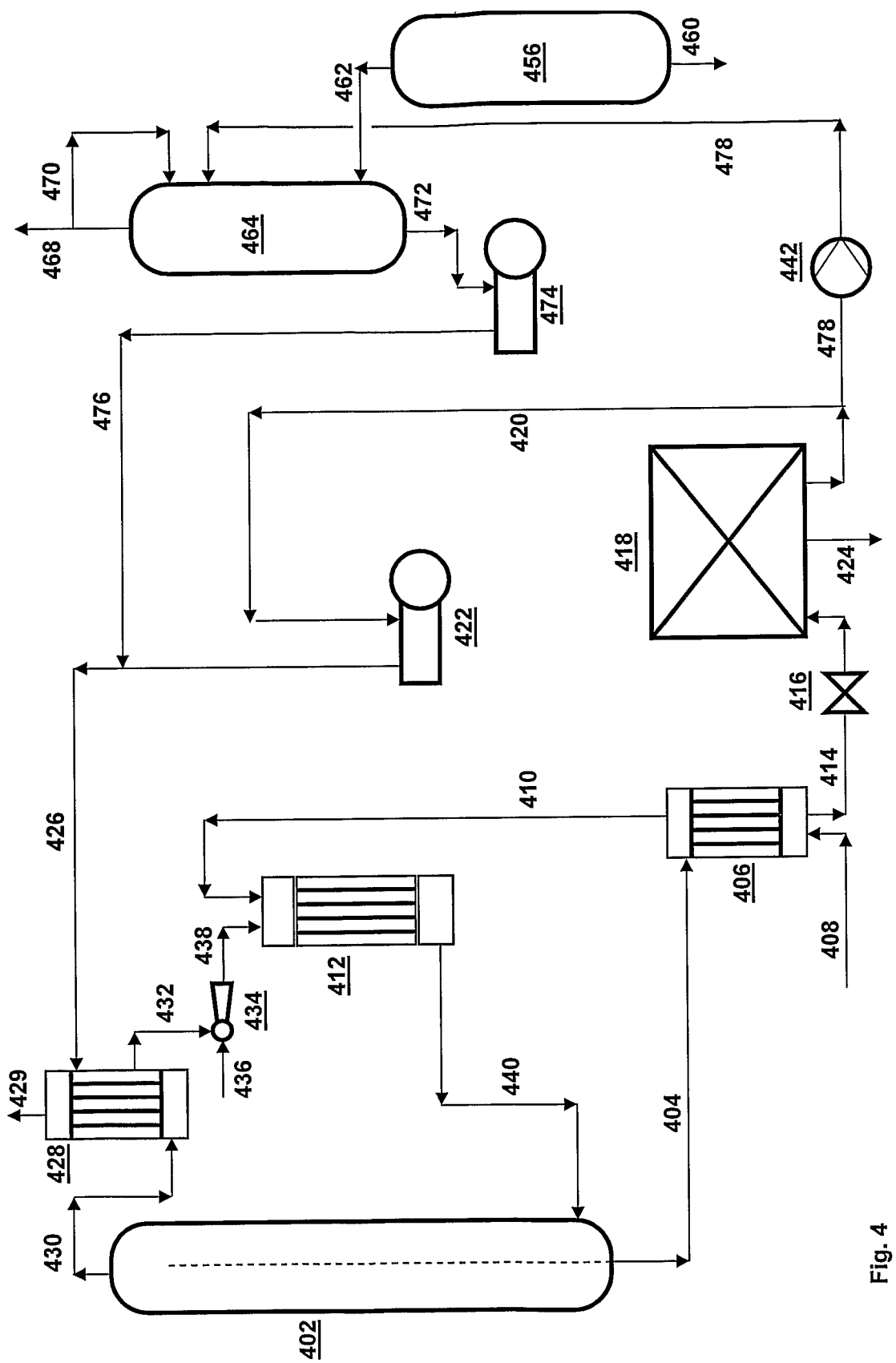
FIG. 4 shows an embodiment according to the invention in which a gas stream, originating from a low-pressure, catalytic process for the preparation of melamine, is absorbed in an aqueous ammonium carbamate stream.

In FIG. 4 a plant and method according to the invention is elucidated. In comparison with the embodiment as elucidated in FIG. 3 a part of the aqueous ammonium carbamate stream coming from the low-pressure recirculation section 418 is supplied to pump 442 and there increased in pressure to about 2 MPa, and then supplied via line 478 to absorber 464 so that this aqueous ammonium carbamate stream can absorb the gas stream supplied via 462 so that a concentrated ammonium carbamate stream is formed, which is discharged via line 472 to compressor 474 to be raised in pressure there and supplied to the high-pressure section of the urea stripping plant, via line 476. In this embodiment of the invention no water is supplied to the stream that is supplied to the urea synthesis section, as is necessary and implemented via line 366 in the known embodiment of FIG. 3.

Figure 5:
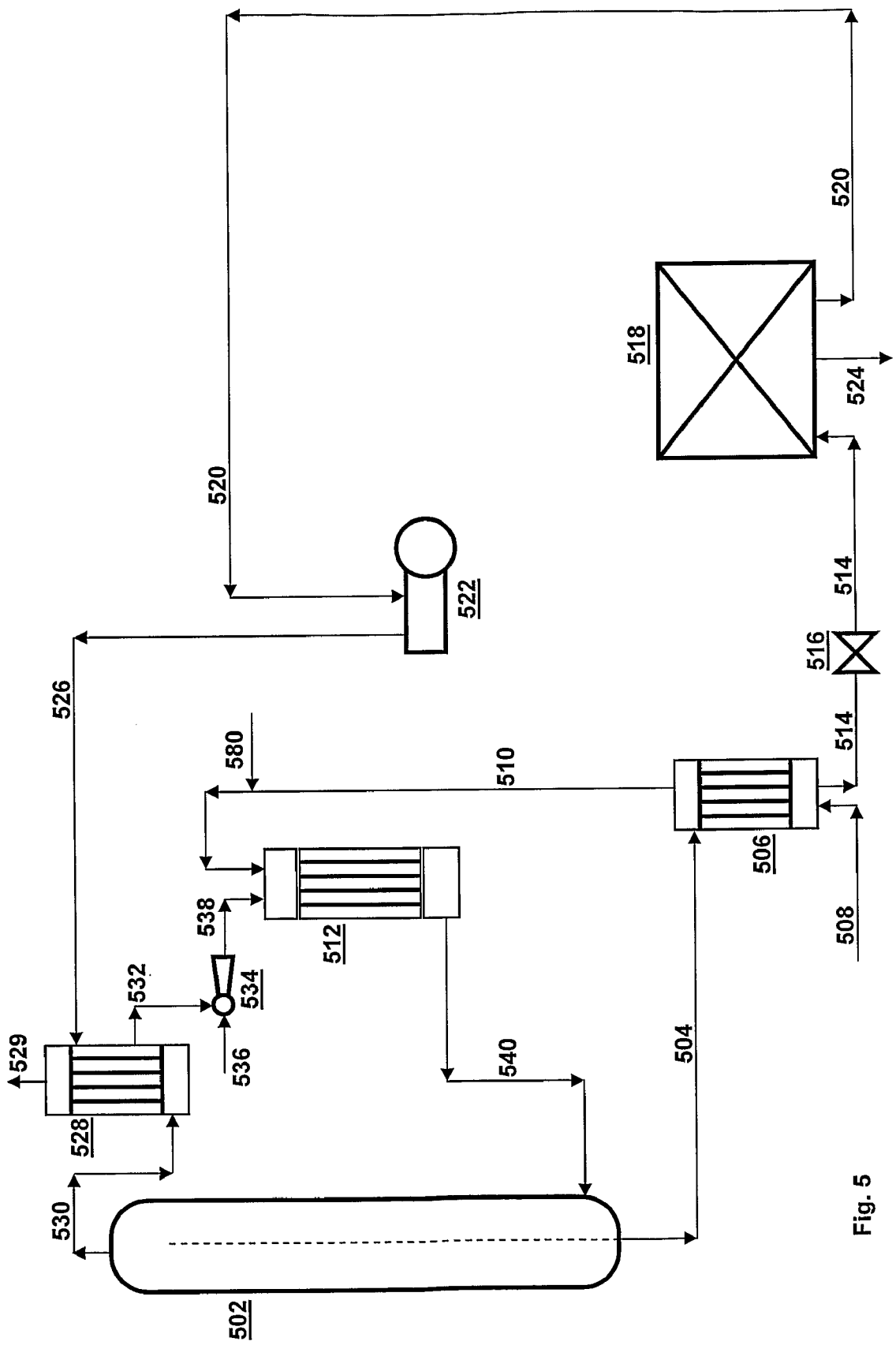
FIG. 5 shows an embodiment according to the state of the art in which a gas stream, originating from a high-pressure non-catalytic process for the preparation of melamine, is introduced directly into the high-pressure section of a urea stripping plant.

FIG. 5 shows an embodiment according to the state of the art as disclosed in WO 98/08808 A1. In this embodiment a gas stream, originating from a high-pressure non-catalytic process for the preparation of melamine, is introduced in gaseous form via line 580 directly into the high-pressure section of a urea stripping plant. The gas stream, having a pressure of about 0.3 MPa above the pressure in the high-pressure section of the urea stripping plant, is introduced in the line running between the stripper and the condenser.

Figure 6:
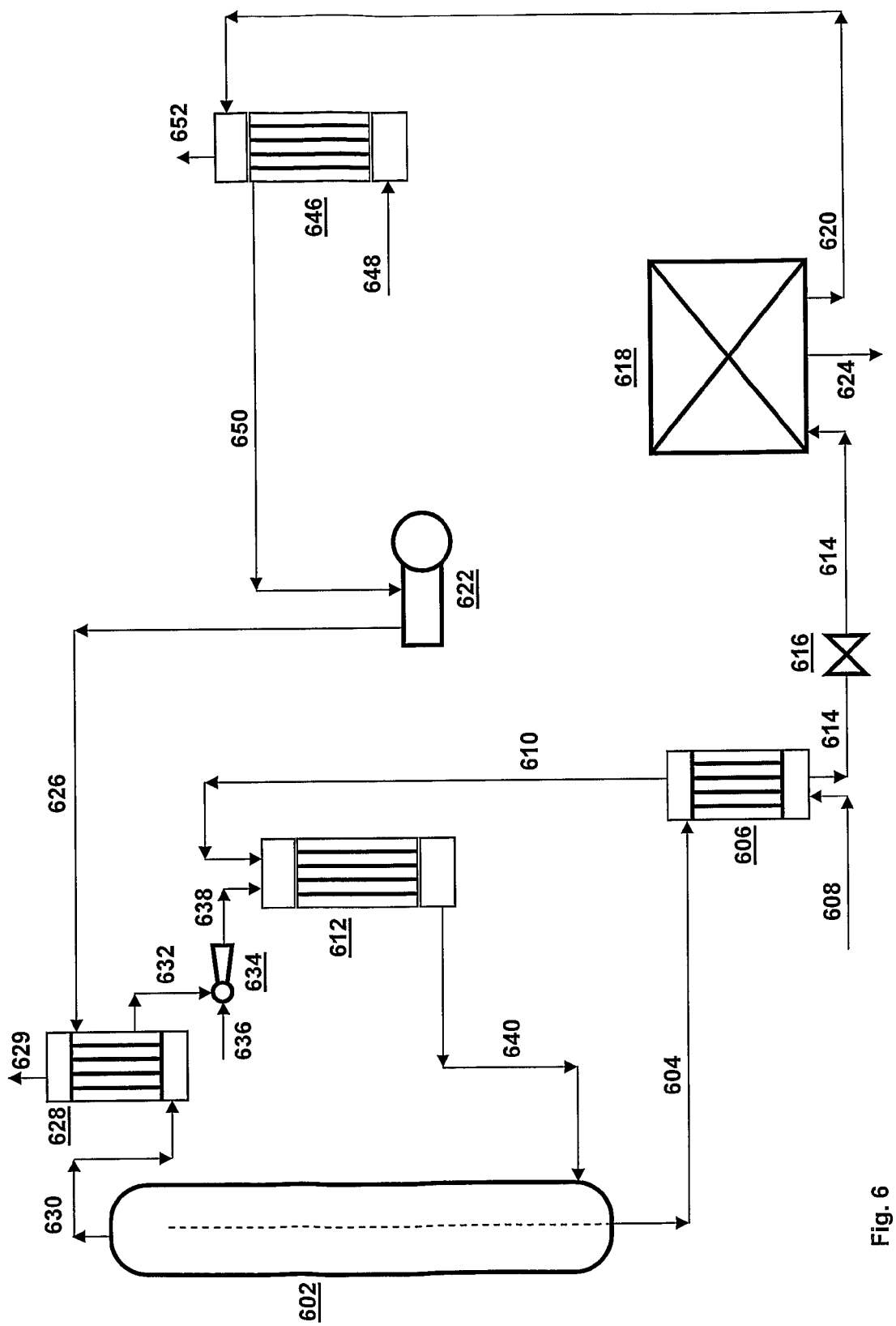
FIG. 6 shows an embodiment according to the stat of the art in which compared to the embodiment according to the invention in FIG. 2 no pressure increase step is executed; instead, an aqueous ammonium carbamate stream is subjected directly to a condensation step.

FIG. 6 shows an embodiment according to the state of the art. Compared to the embodiment according to the invention in FIG. 2, no pressure increase step is executed as in 242; instead, an aqueous ammonium carbamate stream is fed directly from 618 to condenser 646 via line 620 and subjected to a condensation step.

The invention will be elucidated with an example, without being restricted thereto.

EXAMPLE 1

A $CO_2$ stripping process is executed in a urea $CO_2$-stripping plant according to FIG. 2; the plant is operated in such a way that the composition of the aqueous ammonium carbamate stream in line 220 is as follows:

$NH_3$=9,522 kg/h
$CO_2$=7,125 kg/h
$H_2O$=5,344 kg/h

This means that the aqueous ammonium carbamate stream, which has a pressure of 0.4 MPa, contains 24.3 wt. % $H_2O$; this is a value that is representative of practice in stripping plants according to the state of the art as in FIG. 1; in such plants this aqueous ammonium carbamate stream is subsequently increased in pressure and used for the synthesis of urea.

According to the invention the aqueous ammonium carbamate stream is increased in pressure in pump 242 from 0.4 MPa to 1.8 MPa and then has a temperature of 90° C. Subsequently, the aqueous ammonium carbamate stream is supplied to condenser 246 via line 244. Via line 248 a gas stream is supplied to this condenser whose composition is 18,641 kg/h $NH_3$ and 16,082 kg/h $CO_2$. The gas stream originates from a high-pressure process for the preparation of melamine and essentially contains no water. The gas stream is formed in the melamine process at a pressure of 8 MPa. The gas stream is fully absorbed, in a stable manner, in the ammonium carbamate stream in the condenser, as a result of which the concentrated ammonium carbamate stream with the following composition is formed, having a temperature of 120° C. and a pressure of 5.7 MPa:

$NH_3$=28,163 kg/h
$CO_2$=23,207 kg/h
$H_2O$=5,344 kg/h

In order to maintain a temperature of 120° C., a heat exchange is applied; an amount of 56 GJ/h of energy is recovered in this fashion in the form of steam. As a result of the absorption of the gas stream, the relative amount of water has decreased from 23.4 to 9.4 wt. %, without any formation of solids (e.g. solid ammonium carbamate) taking place. Any instabilities in the feed of the gas stream supplied from the melamine process are easily absorbed during the formation of the concentrated ammonium carbamate stream. Thus, no destabilizing influence is transmitted to the high-pressure section of the plant. The concentrated ammonium carbamate stream is supplied to pump 222 via line 250, to be increased in pressure to 14 MPa there.

The invention claimed is:

1. Method for concentrating an aqueous ammonium carbamate stream, which has been formed in a process for the preparation of urea, comprising:
    (a) providing an aqueous ammonium carbamate feed stream that has been formed in a $CO_2$ process for the preparation of urea and has a pressure between 0.20 MPa and 0.9 MPa, a temperature between 35° C. and 95° C., and contains at least 25 wt. % $H_2O$;
    (b) increasing pressure of the aqueous ammonium carbamate feed stream to a pressure between 1.0 MPa and 7 MPa and thereby form an aqueous carbamate stream of increased pressure;
    (c) subjecting the aqueous carbamate stream of increased pressure to a condensation step by contacting the aqueous ammonium carbamate stream of increased pressure with a gas stream, wherein the gas stream has been formed in a process for the preparation of melamine and consists essentially of $NH_3$, $CO_2$ and optionally $H_2O$ and has a lower $H_2O$ content than the aqueous ammonium carbamate stream of increased pressure, to cause the gas stream to be absorbed in the aqueous ammonium carbamate stream of increased pressure in such a way that a concentrated ammonium carbamate stream is formed that contains between 15 and 35 wt. % $H_2O$; and
    (d) separating and discharging the concentrated ammonium carbamate stream.

2. Method according to claim 1, wherein the aqueous ammonium carbamate stream that is introduced into the pressure increase step has a pressure between 0.20 MPa and 0.60 MPa and a temperature between 50° C. and 95° C., and wherein step (b) includes increasing the pressure of the aqueous ammonium carbamate feed stream to between 1 MPa and 7 MPa.

3. Method according to claim 1, wherein step (c) includes performing a heat exchange during the condensation step, said heat exchange being done with the aid of a cooling medium, said cooling medium having a temperature lying between 40° C. and 110° C.

4. Method according to claim 1, wherein
    step (d) includes increasing pressure of the concentrated ammonium carbamate stream to between 12.5 and 20 MPa and supplying the concentrated ammonium carbamate stream of increased pressure to a high-pressure section of a stripping process for the preparation of urea.

5. Method according to claim 4, wherein
    step (a) includes providing an aqueous ammonium carbamate feed stream which has been formed in the $CO_2$ stripping process for the preparation of urea which includes the steps of synthesising urea in a reactor and stripping of the effluent of the reactor in a stripper with $CO_2$, and wherein the synthesizing and stripping steps are carried out in a high-pressure section and at substantially the same pressure of between 12.5 and 20 MPa; and wherein
    step (d) includes increasing pressure of the concentrated ammonium carbamate stream to between 12.5 and 20 MPa and supplying the concentrated ammonium carbamate stream of increased pressure to the said high-pressure section wherein at least the synthesizing and stripping steps of the $CO_2$ stripping process are being carried out.

6. Method according to claim 4, which comprises using fresh $CO_2$ as a stripping agent ($C_S$) in the stripping step, wherein a molar ratio between the $CO_2$ that originates from the process for the preparation of melamine (CM) and the fresh $CO_2$ that is used as stripping agent ($C_S$) is between 0.05 and 3.

7. Method according to claim 1, in which the gas stream has been formed in a catalytic, low-pressure, gas-phase process for the preparation of melamine.

8. Method according to claim 1, in which the gas stream has been formed in a non-catalytic, high-pressure, liquid-phase process for the preparation of melamine.

9. Method according to claim 1, which further comprises at least partially condensing the gas stream prior to being fed to the condensation step (c) to thereby form an intermediate ammonium carbamate stream, and feeding the intermediate ammonium carbamate stream to the condensation step (c).

* * * * *

UNITED STATES PATENT AND TRADEMARK OFFICE
CERTIFICATE OF CORRECTION

| | |
|---|---|
| PATENT NO. | : 7,893,298 B2 |
| APPLICATION NO. | : 11/919991 |
| DATED | : February 22, 2011 |
| INVENTOR(S) | : Mennen et al. |

Page 1 of 1

It is certified that error appears in the above-identified patent and that said Letters Patent is hereby corrected as shown below:

Column 13, line 54, insert --stripping-- between "$CO_2$" and "process".

Signed and Sealed this
Nineteenth Day of March, 2013

Teresa Stanek Rea
*Acting Director of the United States Patent and Trademark Office*